(12) United States Patent
Georgeson et al.

(10) Patent No.: US 9,575,004 B2
(45) Date of Patent: Feb. 21, 2017

(54) AUTOMATED LOW COST METHOD FOR ILLUMINATING, EVALUATING, AND QUALIFYING SURFACES AND SURFACE COATINGS

(71) Applicant: The Boeing Company, Huntington Beach, CA (US)

(72) Inventors: Gary E. Georgeson, Tacoma, WA (US); Scott W. Lea, Renton, WA (US); James J. Troy, Issaquah, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/543,282

(22) Filed: Nov. 17, 2014

(65) Prior Publication Data

US 2016/0139056 A1    May 19, 2016

(51) Int. Cl.
*G01N 21/84* (2006.01)
*G01N 21/88* (2006.01)

(52) U.S. Cl.
CPC ...... *G01N 21/8422* (2013.01); *G01N 21/8851* (2013.01); *G01N 2021/8427* (2013.01)

(58) Field of Classification Search
CPC .............. G01N 21/8422; G01N 21/88; G01N 2021/8861; G01C 21/3638; G01B 11/25; G06T 17/00
See application file for complete search history.

(56) References Cited

U.S. PATENT DOCUMENTS

| | | | | |
|---|---|---|---|---|
| 5,988,862 A * | 11/1999 | Kacyra | ............ | G01B 11/002 382/195 |
| 6,441,896 B1 * | 8/2002 | Field | ............ | G01J 1/4257 356/222 |
| 6,611,617 B1 * | 8/2003 | Crampton | ............ | G01B 11/2518 356/614 |
| 7,859,655 B2 | 12/2010 | Troy et al. | | |
| 8,044,991 B2 | 10/2011 | Lea et al. | | |
| 2004/0057057 A1 * | 3/2004 | Isaacs | ............ | G01B 11/24 356/601 |
| 2011/0075814 A1 * | 3/2011 | Boese | ............ | A61B 6/4007 378/122 |
| 2011/0267453 A1 * | 11/2011 | Matsumoto | ............ | H04N 7/18 348/128 |
| 2012/0230668 A1 * | 9/2012 | Vogt | ............ | G03B 17/561 396/428 |
| 2013/0188059 A1 * | 7/2013 | Georgeson | ............ | G01B 11/24 348/169 |
| 2013/0342824 A1 * | 12/2013 | Ponomarev | ............ | G01B 11/0658 356/51 |
| 2014/0184786 A1 | 7/2014 | Georgeson et al. | | |
| 2016/0025381 A1 * | 1/2016 | Luftglass | ............ | B23P 15/26 126/640 |

* cited by examiner

*Primary Examiner* — Kara E Geisel
*Assistant Examiner* — Maurice Smith
(74) *Attorney, Agent, or Firm* — Parsons Behle & Latimer (57) ABSTRACT

Systems and methods for inspecting a surface are disclosed. A source, detector, a base, a controller, and a processing device are used to collect image data related to the surface and information relating to the location of the image data on the surface. The image data and information relating to location are correlated and stored in a processing device to create a map of surface condition.

19 Claims, 7 Drawing Sheets

AUTOMATED LOW COST METHOD FOR ILLUMINATING, EVALUATING, AND QUALIFYING SURFACES AND SURFACE COATINGS

FIELD OF THE DISCLOSURE

This disclosure relates generally to inspection systems for the inspection of surfaces and surface coatings. In particular, this disclosure relates to inspection systems providing a precise spectrum of electromagnetic radiation at a known position and orientation in order to create an evaluation map of the inspected surface or surface coating.

BACKGROUND

Existing inspection systems and methods for the inspection of surfaces and surface coatings (collectively, "surfaces" as used herein) may suffer from many drawbacks. This is particularly true when the surface to be inspected is fairly large (such as an aircraft) and the spectrum of electromagnetic radiation on the surface may vary with the environment (e.g., indoor versus outdoor).

For example, when painting aircraft it is often common to mix mica into the paint, or to apply a mica coating over the aircraft surface. Uneven mixing or application of the mica can leave the aircraft with a spotted or mottled appearance. This mottling may be difficult to observe under the indoor lighting used in the painting facility and often the mottled appearance does not show until the painting is complete and the aircraft is observed outdoors under natural daylight. It then can be problematic and expensive to re-apply paint or other coatings to alleviate the mottling or other visual defect.

Some existing systems, such as Laser Scanning Confocal Microscopy (LSCM) may be used to inspect surfaces and evaluate whether a defect such as mottling exist, however, performance of LSCM is often a tedious and local measurement that requires access to the plane.

Another proposed solution has been to add lamps to the interior of a structure housing an airplane. Then the aircraft could be painted, or at least inspected, under such lighting. Potential drawbacks of this approach include the relatively high cost of a large scale illumination system, and that the orientation of illumination and imaging is not controlled (i.e., the illumination is primarily from above on the top side of the aircraft) which can leave defects on the underside surfaces undetected. In addition, large scale illumination systems like the above-described one are not practical for inspecting surfaces for defects that are not visible to the human eye (e.g., surface features that require infrared, ultraviolet, or other spectra to observe). Other drawbacks may also exist.

Another potential drawback of existing systems for surface inspection is that it is often difficult to relate inspected surface information to a location on the aircraft, or larger overall surface, for later remediation. For example, when using hand-held imaging tools, the location of the particular defect is not automatically located on the larger surface and requires additional marking or logging of the location of the defect. Other drawbacks may also exist.

Another potential drawback of existing systems is that for irregular, curved, or other non-simple surfaces, it is often difficult to ensure that the angle of incidence for the inspection illumination is at the desired angle of incidence, likewise with the angle of observation of the imaging device (e.g., camera). Improper angle of incidence or observation can yield faulty inspection results. Other drawbacks may also exist.

SUMMARY

Accordingly, the disclosed systems and methods alleviate or eliminate many of the above-noted drawbacks. Other advantages of the disclosed systems and methods also exist.

Disclosed embodiments include an inspection system comprising a source, a detector, a base for locating at least one of the source or detector, a controller in communication with at least the base to communicate location control information that enable the base to locate at least one of the source or detector in response to the location control information; and a processing device for collecting image data from the detector and storing the image data in a manner that correlates the image data with information related to the location of at least one of the source or detector.

In some embodiments the base further comprises a movable base. In further embodiments the movable base further comprises a local positioning system ("LPS" as described below). In still further embodiments the LPS further comprises a wheel assembly that enables the base to become holonomic. In some embodiments the base further comprises a stationary base or a suspended base.

In some embodiments the source comprises a light source.

In some embodiments, the information related to the location of at least one of the source or detector comprises information related to the angle of incidence for the at least one source.

In some embodiments, the information related to the location of at least one of the source or detector comprises information related to the angle of observation for the at least one detector.

In some embodiments, the processing device further correlates the image data with information related to the field of view. In further embodiments, the locations of at least one of the source or detector may be computed as a function of the field of view Also discloses are embodiments for a method for inspecting a surface comprising illuminating a surface with a source, capturing image data related to the surface with a detector, storing, in a processing device, information related to the location on the surface correlated to the captured image data, analyzing the captured image data for surface properties, and storing a result of the analysis in a processing device.

In some embodiments the method may further comprise displaying the result of the analysis on a display.

In some embodiments, the method may further comprise relocating at least one of the source or detector, capturing additional image data related to the surface, and storing, in the processing device, information related to the location on the surface that correlates to the additional captured image data.

In further embodiments the relocating at least one of the source or detector is carried out by an LPS. In still further embodiments the method further comprises capturing information related to the location of at least one of the source or detector.

In still further embodiments, the capturing information related to the location of at least one of the source or detector comprises capturing information related to the angle of incidence for the at least one source.

In still further embodiments, the capturing information related to the location of at least one of the source or detector comprises capturing information related to the angle of observation for the at least one detector.

In still further embodiments, the method further comprises storing information related to the field of view.

In some embodiments, the result of the analysis and the information related to the location on the surface are used to form a map of the surface condition.

Other embodiments are also disclosed.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

Some embodiments of the disclosed systems and methods incorporate an LPS. Various features and capabilities of an LPS, as well as systems and methods for pointing an instrument at a target, and correlating inspection information with computer-aided design ("CAD") data, are disclosed in related U.S. Pat. No. 7,859,655, titled "Method Involving A Pointing Instrument And A Target Object," U.S. Pat. No. 8,044,991, titled "Local Positioning System and Method," and U.S. Pat. No. 8,249,832, titled "Correlation Of Inspection Information And Computer-Aided Design Data For Structural Assignment," which are all herein incorporated by reference in their entirety.

Figure 1:
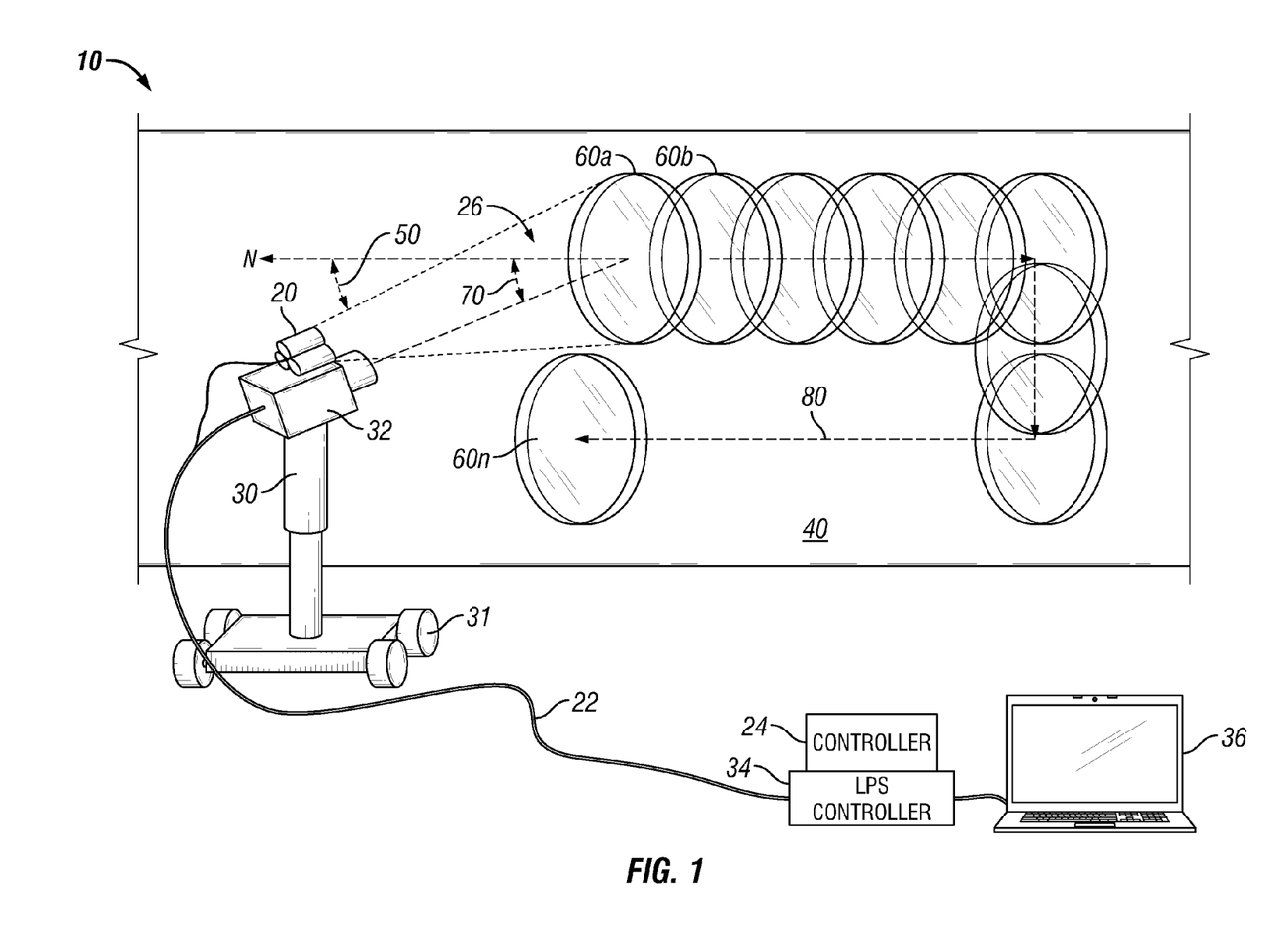
FIG. 1 is a schematic illustration of some embodiments of the disclosed inspection system implementing an embodiment of a mobile base LPS.

FIG. 1 is a schematic illustration of some embodiments of the disclosed inspection system 10 implementing an embodiment of a mobile base LPS. As shown, embodiments of the inspection system 10 may comprise an illumination or electromagnetic radiation source 20, an source controller 24, and an LPS. Embodiments of an LPS may comprise, at least one moveable base 30, at least one detector 32, at least one LPS controller 34, and at least one processing unit 36.

In some embodiments, electromagnetic radiation source 20 may comprise any suitable source of radiation, or illumination, sufficient to cover the inspected surface 40 and is typically chosen to reveal the defects, irregularities, problems, or characteristics of the inspected surface 40. For example, the source 20 may comprise visible light lamps selected to produce AM1.5 full spectrum light (which may be filtered to match MIL-STD 810G, Method 505, Table 505.5-1), or the like. In other embodiments, source 20 may comprise infra-red (IR) irradiators, ultraviolet (UV) irradiators, x-ray sources, ultrasound sources, LCD projectors, millimeter wave, microwave, terahertz radiation, ionization radiation (like backscatter x-ray), or the like. For embodiments of surfaces 40 or sources 20 for which the electromagnetic radiation penetrates the surface 40 some different operational requirements and components may be used as discussed in connection with FIG. 6 below.

In some embodiments, the source 20 may comprise at least one source (i.e., a lamp, or bulb, or other emitter), and in other embodiments multiple sources may be implemented. Likewise, while source 20 is shown in FIG. 1 as co-located with the detector 32, it need not be and other locations for the source 20 are possible.

In some embodiments, a communication path 22 is provided over which source 20 may communicate with source controller 24. Communication path 22 may comprise any suitable path for source controller 24 and source 20 to communicate at least some of the information useful in operating the source 20. Communication path 22 may comprise a wired, wireless, or other suitable communication path.

As noted above, embodiments of the inspection system 10 may also comprise an source controller 24 which may comprise suitable programming (including, but not limited to software, firmware, or the like), and associated hardware (e.g., lenses, apertures, filters, actuators, or the like) used to control the operation of the source 20. Source controller 24 may also comprise a "stand-alone" unit or it may comprise a component of LPS controller 34. In some embodiments, source controller 24 may comprise a distributed system with portions of the controller 24 located at or near source 20 and portions located at or near the LPS controller 34. Other configurations are also possible.

Source controller 24 provides commands or instructions to source 20 (and, potentially, other inspection system 10 components as described herein) in order to control the characteristics of the electromagnetic radiation 26 being produced by the source 20. For example, the duration, size, intensity, frequency, wavelength, focus, and other characteristics may be controlled or varied under operation of the source controller 24.

Embodiments of the inspection system 10 also comprise a movable base 30. For embodiments where movable base 30 may comprise an LPS, additional details may be found in the related U.S. Pat. No. 7,859,655, U.S. Pat. No. 8,044,991, and U.S. Pat. No. 8,249,832, which are incorporated herein by reference. In general, movable base 30 allows for the locating of one or more of detector 32, source 20, or both. As used herein, "locating," "location," "locatable," "relocated," and "relocating," or the like, generally mean any or all of the position, orientation, alignment, and movement of the component described.

As described more completely in the above-described related patents, the angle of incidence 50 for the electromagnetic radiation 26, the angle of observation 70, and the location of the movable base 30 with respect to the inspected surface 40 may be controlled through operation of movable base 30 and LPS controller 34. As shown in FIG. 1, embodiments of movable base 30 may comprise wheels 31 that enable the base 32 to become holonomic, such as Mecanum wheels, omni wheels, or poly wheels, which allow location control of the movable base 30 as desired. As disclosed below, other types of movable base 30 are also possible.

As also shown in FIG. 1, inspection system 10 may also comprise an detector 32 that is suitable to detect the electromagnetic radiation 26 produced by source 20 and reflected, refracted, or otherwise received from the inspected surface 40. For example, for embodiments of inspection system 10 that implement a visible light source 20, the detector 32 may comprise a camera (film, tape, digital, CCD, or otherwise).

In some embodiments, detector 32 and movable base 30 communicate with LPS controller 34 via previously described communication path 22. Embodiments of LPS controller 34 may comprise suitable programming (including, but not limited to software, firmware, or the like), and associated hardware (e.g., actuators, motors, transducers, or the like) used to control the operation of the LPS components (e.g., movable base 30, detector 32, or the like). LPS controller 34 may also comprise a "stand-alone" unit or it may be combined with source controller 24. In some embodiments, LPS controller 34 may comprise a distributed system with portions of the LPS controller 34 located at or near the LPS components (e.g., 30, 32, etc.) and portions located at or near the LPS controller 34. In some embodiments, some, or all, of the LPS controller 34 may reside on processing device 36. Other configurations are also possible.

As shown in FIG. 1, a processing device 36 communicates with source controller 24 and LPS controller 34. Processing device 36 may comprise a personal computer (PC), laptop, tablet, or any other microprocessor based device capable of performing the functions described herein. As noted previously, at least some portions of source controller 24 and/or LPS controller 34 may reside on processing device 36 in some embodiments to enable coordinated operation of the respective systems. Likewise, portions of processing device 36 may be distributed or located elsewhere in the system 10. Processing device 36 may also comprise suitable programming for image analysis, and for reporting inspection results.

One exemplary goal of the disclosed systems and methods is to acquire images of specific target areas on the surface 40 of an object using known electromagnetic radiation intensities and wavelengths, and at known angles of incidence and observation. Then analyze the resulting image data using image processing techniques to determine the characteristics of, or whether any problem exist with, the surface 40. Other goals may also achieved by the disclosed systems and methods.

One method of operation for embodiments like the one shown in FIG. 1 is as follows: electromagnetic radiation 26 is emitted from source 20 under the control of source controller 24 and, potentially, processing device 36. Electromagnetic radiation 26 is emitted with a known angle of incidence (generally indicated at 50 as being measured with respect to a coordinate system of the surface 40, such as a normal vector N perpendicular to the surface 40) onto inspected surface 40 forming an illuminated portion 60a. The known angle of incidence 50 is known because it may be a predetermined value assigned by programming in the controller 24 and/or processing device 36, or it may be known because it is determined from data acquired from the LPS. Likewise, the angle of observation 70 for the detector 32 may be known or determined from the programming assigned value or from acquired data. In some embodiments, the location of the intersection of the aiming vector on a target object may be specified, and the controller 34 may calculate what the angles of incidence 50 and angles of observation 70 preferably may be. In other embodiments, if a specific angle of incidence 50 and angle of observation 70 are required for a specific location on the target, the moveable base 30 may move to a relative location in order to achieve the desired angles. In general, acquiring images of specific locations on the target at specific angles of incidence 50 and observation 70 can depend on where the source(s) 20 and detector(s) 32 are located.

In embodiments where illuminated portion 60a does not cover the entirety of inspected surface 40, or for other reasons, it may be desirable to relocate the source 20 to form another illuminated portion 60b. Relocation of source 20 may be accomplished by locating with the LPS (e.g., by translating, rotating, tilting, or otherwise moving movable base 30, by changing the angle of incidence 50, or the like). Locating may continue along inspection path 80, forming additional illuminated portions along the path as indicated in FIG. 1 and continuing through to illuminated portion 60n. While inspection path 80 is shown as generally rectangular and clockwise, the disclosed systems and methods are not so limited and any suitable inspection path 80 may be used.

In accordance with the disclosed systems and methods, image data from the illuminated portion 60a, 60b, . . . , 60n, may be captured by detector 32 and recorded, and stored in processing device 36, along with data from the LPS corresponding to the location on the inspected surface 40 of the detected electromagnetic radiation. In some embodiments inspected surface 40 may comprise an aircraft body or component.

Figure 2:
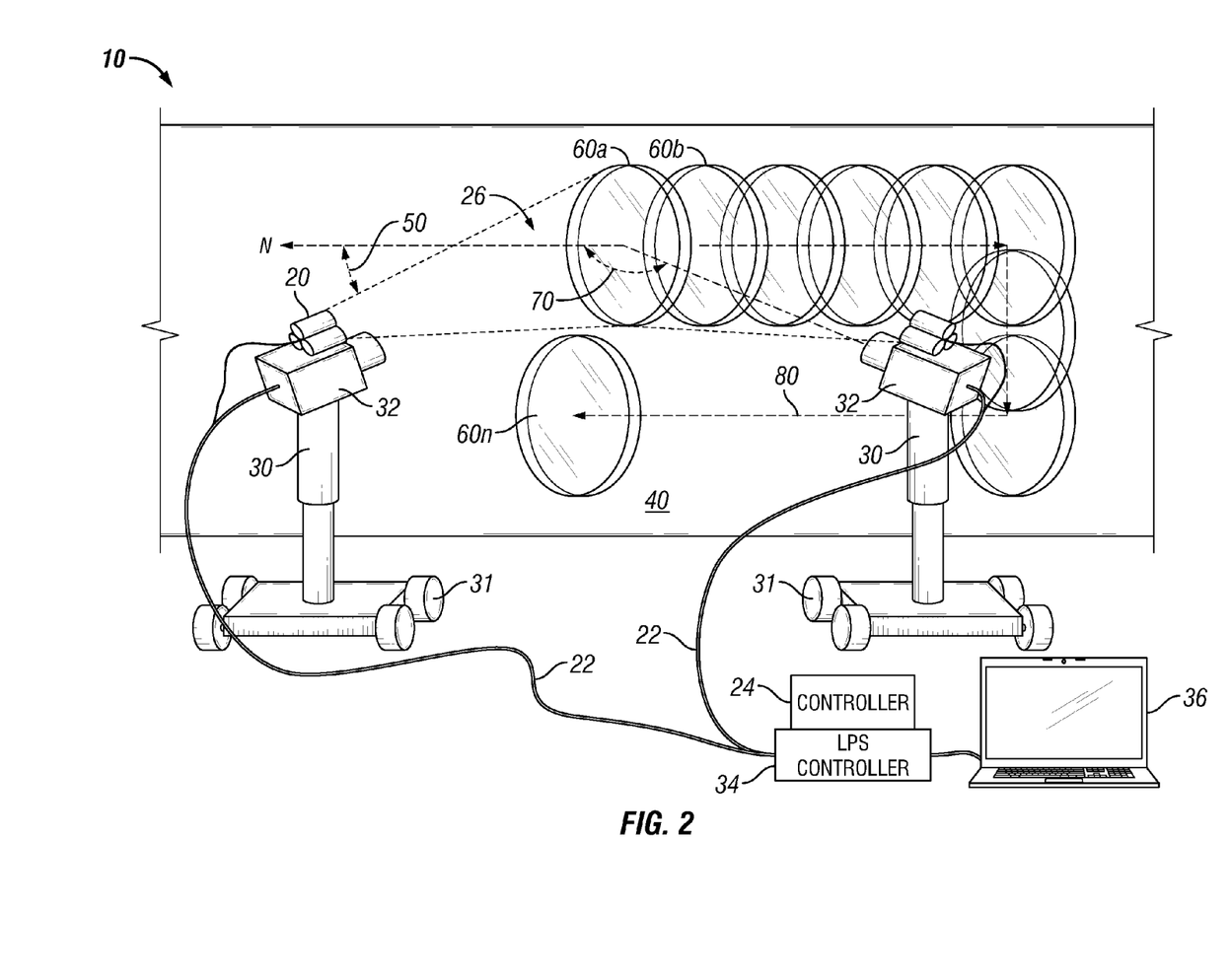
FIG. 2 is a schematic illustration of some embodiments of the disclosed inspection system implementing separate incidence and observation angles.

FIG. 2 is a schematic illustration of some embodiments of the disclosed inspection system implementing separate incidence and observation angles. As shown in FIG. 2, where like numbers refer to like elements, for some embodiments it may be preferable to separate the source 20 and the detector 32 and locate them each on a movable base 30. In this manner, electromagnetic radiation 26 at a predetermined angle of incidence 50 may be observed at another predetermined angle of observation 70. Of course, both the source 20 and detector 32 are connected to the appropriate controllers (e.g., 24, 34) and processing device 36 for operational control and inspection data collection. Other configurations are, of course, also possible.

Figure 3:
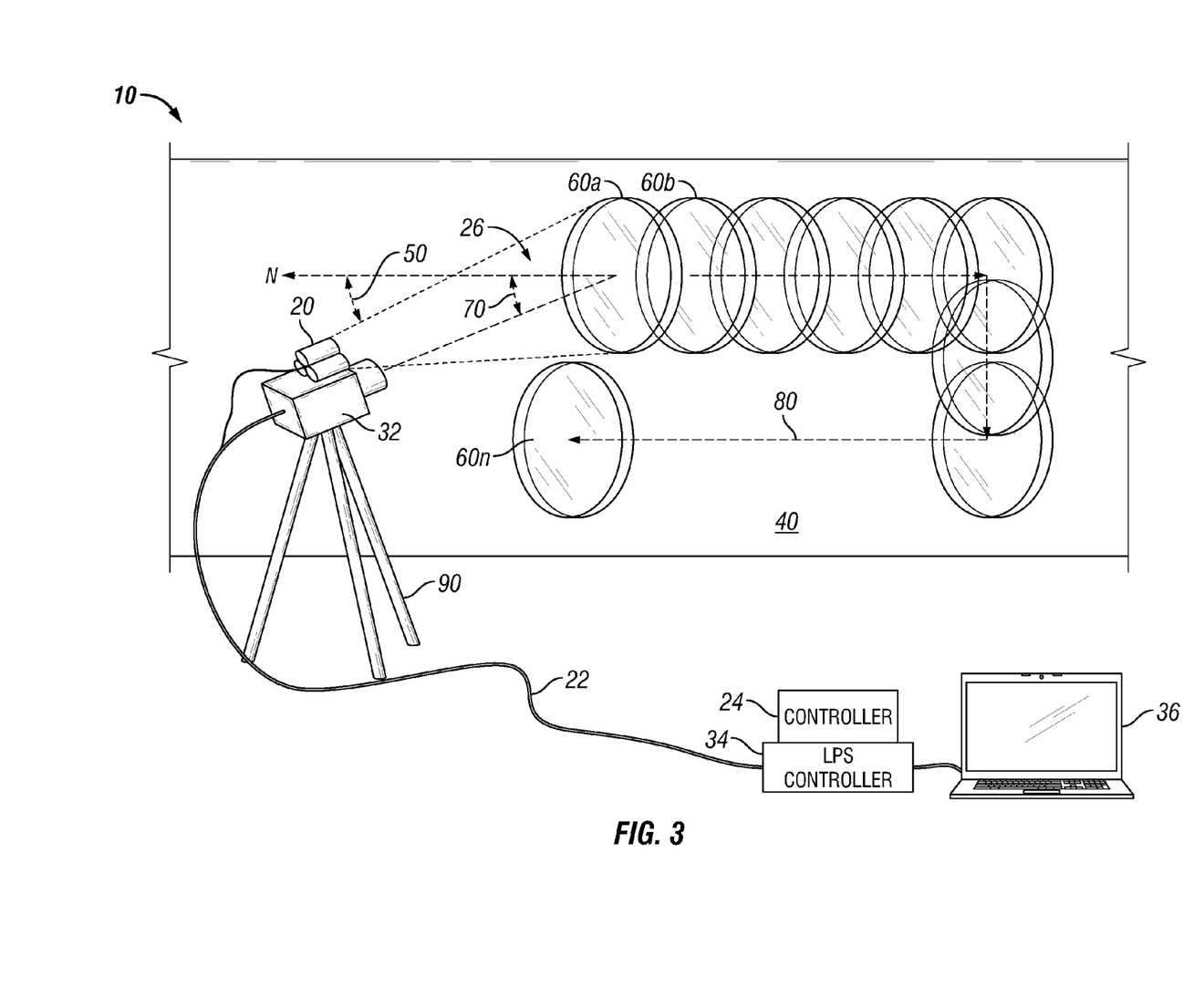
FIG. 3 is a schematic illustration of some embodiments of the disclosed inspection system implementing a stationary base.

FIG. 3 is a schematic illustration of some embodiments of the disclosed inspection system 10 implementing a stationary base 90. While depicted generally as a tripod, the disclosed systems and methods are not so limited and any suitable stationary base 90 may be used. Further, while stationary base 90 is considered stationary, in that it does not move once placed in position, for some embodiments stationary base 90 may still be locatable in the sense that it may be adjustable in one or more directions, and, further, detector 32 and source 20 may still be tilted, rotated, translated, or the like relative to the stationary base 90. For embodiments that implement a stationary base 90, the angle of incidence 50 and angle of observation 70 may change as the inspection path 80 is followed and processing device 36 may be appropriately programmed to account for the changes.

Figure 4:
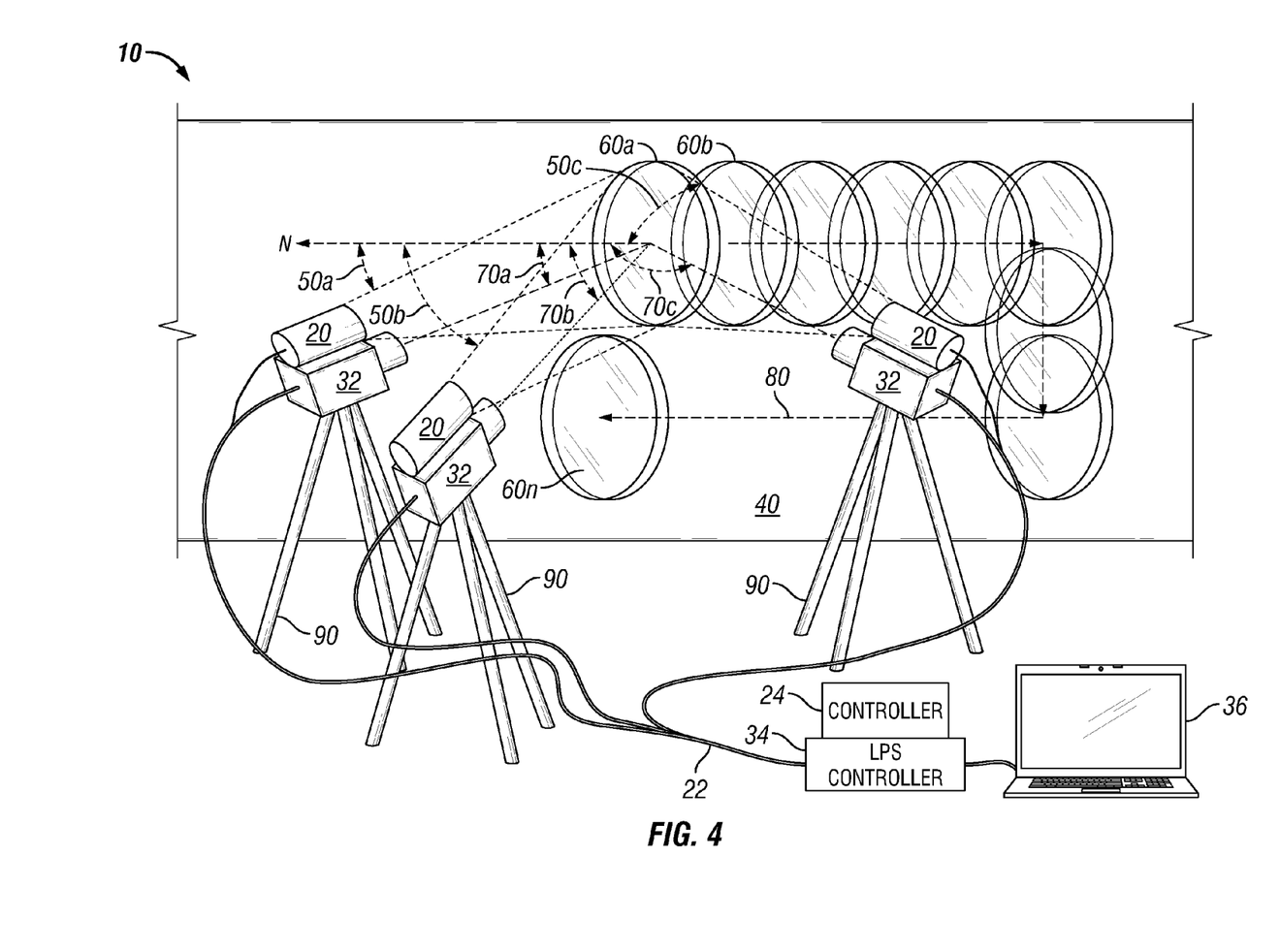
FIG. 4 is a schematic illustration of some embodiments of the disclosed inspection system implementing multiple sources and detectors.

FIG. 4 is a schematic illustration of some embodiments of the disclosed inspection system 10 implementing multiple sources 20 and detectors 32. For some applications it may be desirable to illuminate the inspected surface 40 from a variety of angles of incidence (e.g., 50a, 50b, 50c) and to collect inspection data from a variety of angles of observation (e.g., 70a, 70b, 70c). Further, in multi-source embodiments like the one shown in FIG. 4, it is possible to implement a different wavelength source 20 (e.g., UV, IR, different visible colors, or the like) on each base 90 or combinations thereof. Detectors 32 may also detect in different source-corresponding wavelengths, or may detect in an appropriate combined or common wavelength as desired. Likewise, while FIG. 4 depicts stationary bases 90, movable bases 30 (as shown in FIGS. 1-2), or suspended bases 94 (as shown in FIG. 5) may also be implemented.

Figure 5:
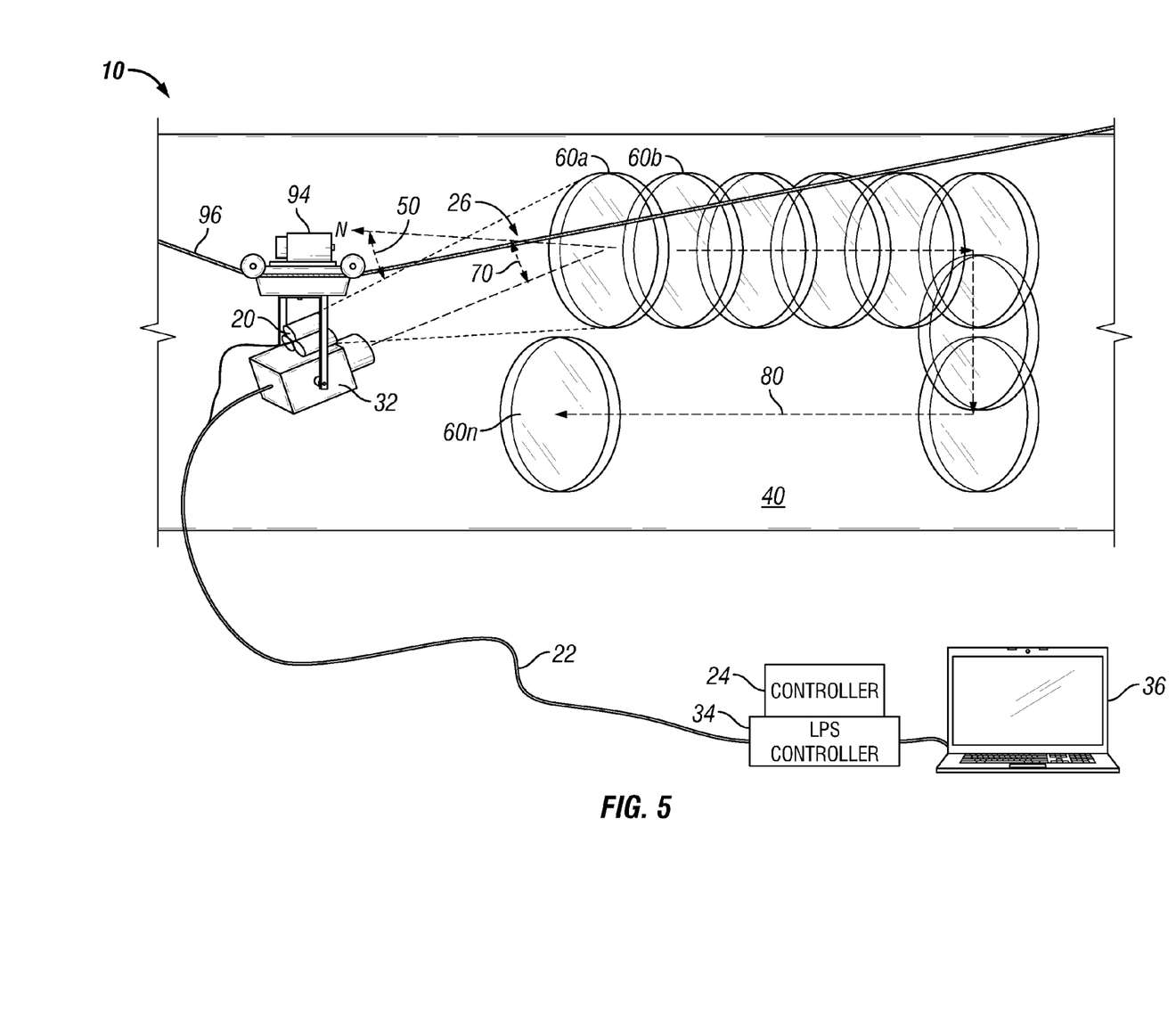
FIG. 5 is a schematic illustration of some embodiments of the disclosed inspection system implementing a suspended source and detector.

FIG. 5 is a schematic illustration of some embodiments of the disclosed inspection system 10 implementing a suspended source 20 and detector 32. As shown, a suspended source 20 and detector 32 embodiments may comprise a suspended base 94 that can travel over suitable wires, or cables 96. Suspended base 94 may comprise appropriate reels, motors, gearing, or the like in communication with the LPS controller 34 to allow location of the source 20 and detector 32 as desired. Other configurations are also possible.

Figure 6:
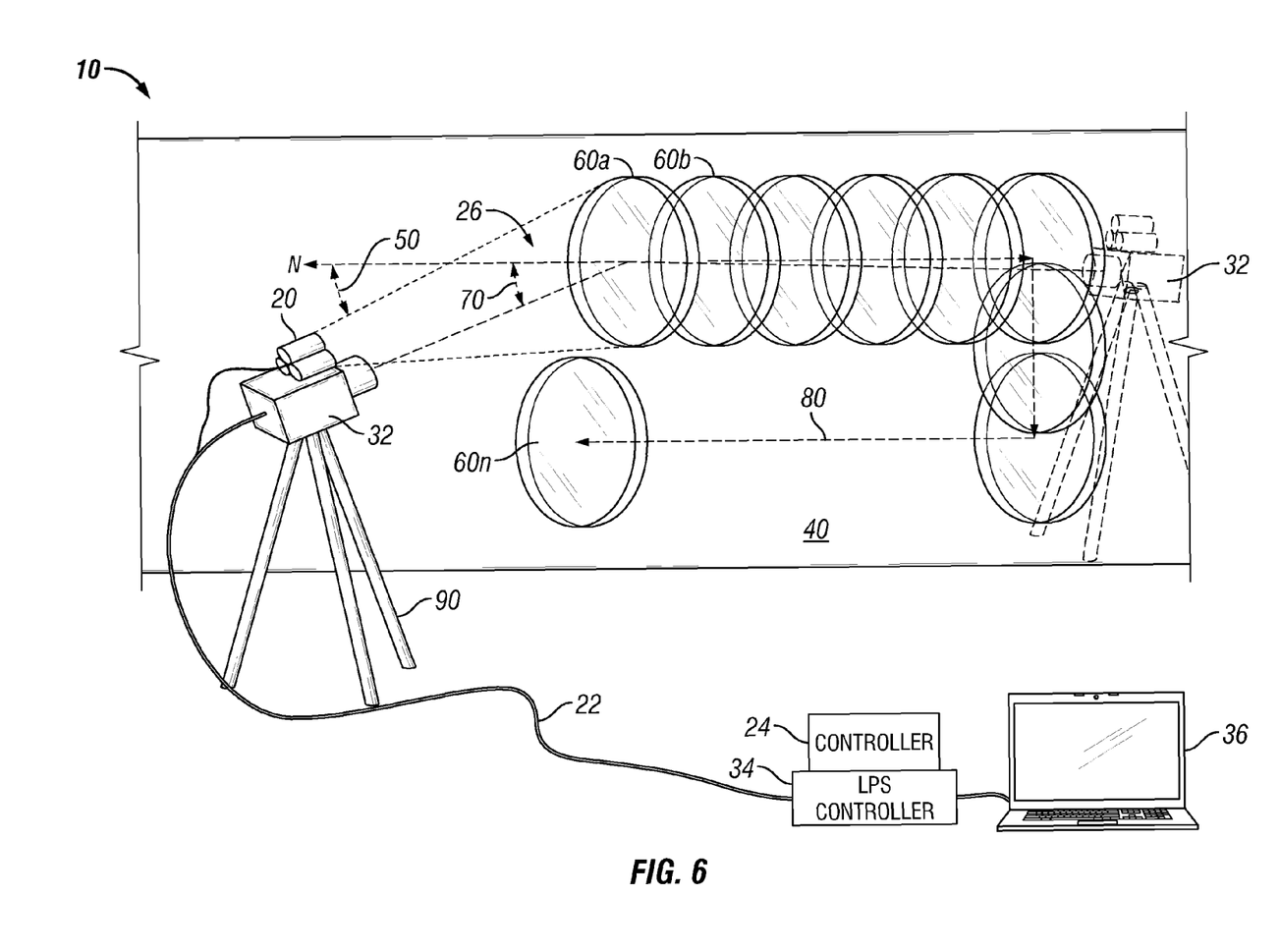
FIG. 6 is a schematic illustration of some embodiments of the disclosed inspection system implementing a penetrating source 20 or a transparent surface 40.

FIG. 6 is a schematic illustration of some embodiments of the disclosed inspection system implementing a penetrating source 20 or a transparent surface 40. For embodiments, such as the one illustrated in FIG. 6, where the electromagnetic radiation 26 penetrates through surface 40 it may be desirable to locate the source 20 and the detector 32 on opposing sides of the surface 40. In addition, the LPS controller 34 and/or the processing device 36 may be programmed to account for penetration of the electromagnetic radiation 26, for example, by adjusting the observation angle 70 to account for refraction, or other redirection, of the electromagnetic radiation 26 as it penetrates the surface 40, and/or to account for any change in angle of refraction or redirection due to the properties of the material comprising surface 40.

Figure 7:
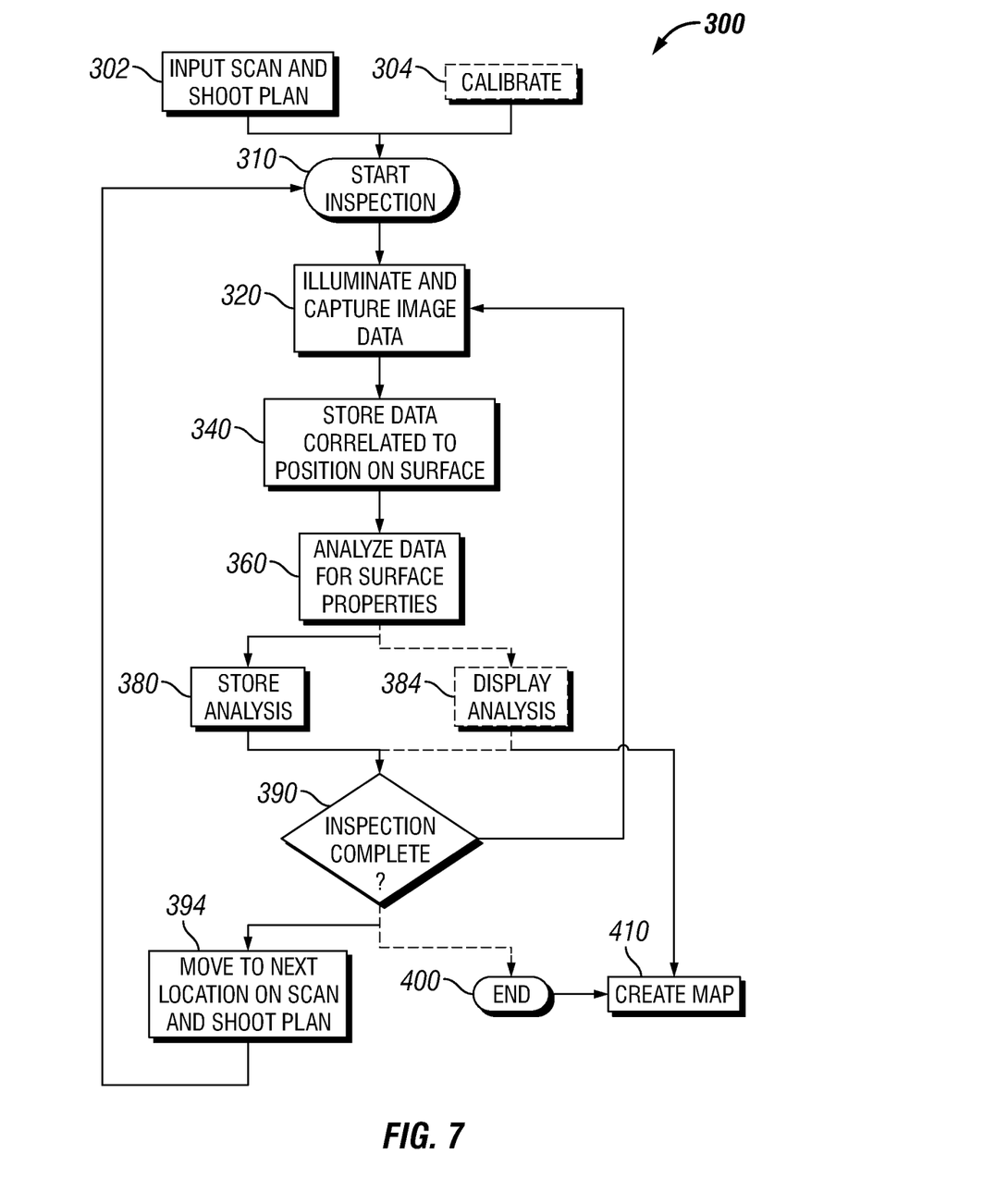
FIG. 7 is a schematic flow chart indicating some embodiments of a method for performing a surface inspection in accordance with the disclosure.

FIG. 7 is a schematic flow chart indicating some embodiments of a method 300 for performing a surface inspection in accordance with the disclosure. As shown, at 302 in some embodiments, a scan and shoot plan may be loaded into LPS controller 34 and/or processing device 36. In general, a scan and shoot plan may comprise any suitable plan to efficiently and accurately scan the inspected surface 40 of interest. A scan and shoot plan typically includes a plan for the scan area, inspection points, and scan path to be conducted, as well as, the angles and distances for sending and receiving information for each inspection point in the plan. In general, an LPS motion sequence plan involves calculating target points on surface 40 defined in a target object coordinate system arranged in such a way as to have overlapping regions (e.g., 60a, . . . , 60n) based on the size of the projected illumination region and the size and shape of the image data, or electromagnetic radiation data, captured by the camera or detector 32. The size and shape of the projected electromagnetic radiation 26 and the captured data depends on the angle of incidence 50 and observation 70 as well as the field of view of both the source 20 and detector 34.

In general, this is a non-trivial geometry problem, since the size of the illumination projection region (e.g., 60a, . . . , 60n) on the surface 40 changes as the angles of incidence 50 and observation 70 change. For movable base 30 embodiments that keep the same angle of incidence 50 for each region (60a, . . . , 60n), the problem is simpler, but still has nonlinearities associated with surface 40 curvature that may need to be addressed.

In some embodiments, a solution can be computed automatically using iteration and 3D simulation. Staring with an equally spaced pattern (60a, . . . , 60n), the coverage areas are checked and the target point spacing is adjusted or the field of view of the source 20 and detector 32 are adjusted to achieve full coverage with minimal overlap.

As also indicated at 304, some embodiments may optionally include another initial step which is to calibrate LPS to the target object's coordinate system, for example using a 3-point method as described in the above-incorporated U.S. Pat. No. 7,859,655. Other calibration methods may also be used.

Next, as indicated at 310 the inspection may begin. The surface 40 may be illuminated by a suitable source 20 and image data of the surface 40 may be captured as indicated at 320 by a suitable detector 32. As used herein, image data refers to whatever characteristics of the detected electromagnetic radiation are relevant to the inspection of the surface. For example, in cases where the inspection is for visible appearance of the surface (e.g., surface paint) the image data may comprise a photograph. In cases where absorption of UV radiation is relevant to the inspection, the image data may comprise detected UV absorption levels (e.g., intensities). Other types of image data are also possible.

Illumination may be accomplished by a suitable source 20 selected in accordance with the selected detector 32 and properties of the surface 40 to be inspected. For example, an IR source 20 may be used in conjunction with an IR detector 32 in order to evaluate surface 40 with respect to their response to illumination in the IR spectrum. Of course, visible light sources 20, and "traditional" detectors 32 (i.e., cameras) may also be used to inspect the visual aspects of a surface 40. Other sources 20, such as UV, x-ray, or the like, and corresponding detectors 32 may also be used.

In some embodiments, in particular, those that implement an LPS, the image data captured in 320 may be stored in a memory device (e.g., a memory associated with processing device 36), in a manner that correlates the location on the surface 40 to the image data stored as indicated at 340. In addition, embodiments that implement an LPS may also store at 340 angle of incidence 50 and observation 70 data, as well as field of view of the source 20 and detector 32 for each region (60a, . . . , 60n).

Next, as indicated at 360, analysis programming in processing device 36 is used to analyze the image data and evaluate the surface 40 in accordance with the purpose of the inspection. For example, for a painted surface 40, image analysis programming may be used to evaluate the image data for evidence of mottling, or the like, by comparing the collected image data and angle of incidence and observation to stored reference values or the like. This may include image processing to compare values such as color and intensity. Other analysis methods are also possible and will vary with the intended purpose of the inspection and type of image data collected.

As indicated at 380, the result of the image data analysis may be stored (e.g., in a memory associated with processing device 36) for later use and retrieval. The result of the analysis may comprise any suitable information relevant to the inspection and may range from a simple "pass" or "fail" indication to more complex notations of surface 40 characteristics or the like. Optionally, as indicated at 384, the results of the analysis may be displayed to the inspection system 10 operators, for example, on a display associated with processing device 36, or via some other networked processing device.

As indicated at 390, the LPS controller 34 and/or programming on processing device 36 evaluate whether the scan and shoot plan has completed. If not, the process may return to the illumination and data capture step 320 and repeat another illumination and data capture process (possibly using different electromagnetic radiation wavelengths, duration, intensities, angles of incidence, angles of observation, or the like).

As also indicated at 390, another result of the "is inspection complete" analysis may be to position the inspection system 10 (e.g., using movable base 30 under control of LPS controller 34 and/or processing device 36) to the next location on surface 40 to be inspected and being the inspection of the new location by returning to step 310 as indicated at 394. As also indicated, this process may repeat until the inspection is determined to have completed and then the process will end as indicated at 400.

By storing the collected image data correlated to the LPS data indicating the location on the inspected surface 40, it is possible to create a "map," as indicated at 410, of the surface 40 and any defects or conditions requiring repair or other remediation. As indicated, creation of the map may occur after the end 400 of the inspection, or may be built additively after each analysis iteration. Other methods for creating the map are also possible. The map may also be combined or overlaid with other data (such as 3D CAD data to create a 3D model of the surface 40) to facilitate the creation of maintenance, repair, or other reports. By using the underlying 3D model of the target object, the shape factor associated with each region on the target object may also be used in the analysis of the image data.

Although various embodiments have been shown and described, the present disclosure is not so limited and will be understood to include all such modifications and variations are would be apparent to one skilled in the art.

What is claimed is:

1. An inspection system comprising:
   a source including visible light lamps selected to produce a spectrum of light that enables the observation of mottling due to an irregular mixture of mica, wherein the spectrum of light is AM1.5 full spectrum light;
   a detector;
   a base for positioning at least one of the source or detector;
   a controller in communication with at least the base to communicate location control information to the base to enable control of a location of at least one of the source or detector; and
   a processor device for collecting image data from the detector and storing the image data in a manner that correlates the image data with information related to the location of at least one of the source or detector, the processor device storing reference data to enable evaluation of the image data by comparing a property of the image data to the stored reference data.

2. The inspection system of claim 1 wherein the base further comprises a movable base.

3. The inspection system of claim 2 wherein the movable base further comprises a local positioning system.

4. The inspection system of claim 3 wherein the local positioning system further comprises a wheel assembly that enables holonomic operation of the moveable base.

5. The inspection system of claim 1 wherein the base further comprises a stationary base.

6. The inspection system of claim 1 wherein the base further comprises a suspended base.

7. The inspection system of claim 1 wherein the source enables adjustment of a target point or a field of view of the source based on a 3D simulation of a surface.

8. The inspection system of claim 1 wherein the information related to the location of at least one of the source or detector comprises information related to the angle of incidence for the at least one source.

9. The inspection system of claim 1 wherein the information related to the location of at least one of the source or detector comprises information related to the angle of observation for the at least one detector.

10. The inspection system of claim 1 wherein the processor device further correlates the image data with information related to the field of view.

11. The inspection system of claim 1 wherein the locations of at least one of the source or detector may be computed as a function of the field of view.

12. A method for inspecting a surface comprising:
    illuminating a surface with a source including visible light lamps selected to produce a spectrum of light that enables the observation of mottling due to an irregular mixture of mica wherein the spectrum of light is AM1.5 full spectrum light;
    capturing image data related to the surface with an detector;
    storing, in a processor device, information related to the location on the surface correlated to the captured image data;
    analyzing the captured image data for surface properties that evidence mottling; and
    storing a result of the analysis in a processor device.

13. The method of claim 12 where the result of the analysis and the information related to the location on the surface are used to form a map of the surface condition.

14. The method of claim 12 further comprising:
    relocating at least one of the source or detector;
    capturing additional image data related to the surface; and
    storing, in the processor device, information related to the location on the surface that correlates to the additional captured image data.

15. The method of claim 14 wherein relocating at least one of the source or detector is carried out by a local positioning system.

16. The method of claim 14 further comprising:
    capturing information related to the location of the at least one of the source or detector.

17. The method of claim 16 wherein capturing information related to the location of at least one of the source or detector comprises capturing information related to the angle of incidence for the at least one source.

18. The method of claim 16 wherein capturing information related to the location of at least one of the source or detector comprises capturing information related to the angle of observation for the at least one detector.

19. The method of claim 16 further comprising storing information related to the field of view.

* * * * *